(12) United States Patent
Hur et al.

(10) Patent No.: US 9,739,766 B2
(45) Date of Patent: Aug. 22, 2017

(54) CELL MODEL FOR NEOVASCULAR DISEASES USING EBV-INFECTED HUMAN CORNEAL EPITHELIAL CELLS

(71) Applicant: INJE UNIVERSITY INDUSTRY-ACADEMIC COOPERATION FOUNDATION, Gyeongsangnam-do (KR)

(72) Inventors: Dae Young Hur, Busan (KR); Ga Bin Park, Busan (KR); Yeong Seok Kim, Busan (KR); Dae Jin Kim, Seoul (KR); Seong Han Kim, Busan (KR); Hyun Kyung Lee, Busan (KR); Jae Wook Yang, Busan (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 0 days.

(21) Appl. No.: 14/894,522

(22) PCT Filed: Dec. 18, 2013

(86) PCT No.: PCT/KR2013/011805
§ 371 (c)(1),
(2) Date: Nov. 29, 2015

(87) PCT Pub. No.: WO2014/193061
PCT Pub. Date: Dec. 4, 2014

(65) Prior Publication Data
US 2016/0116458 A1 Apr. 28, 2016

(30) Foreign Application Priority Data

May 30, 2013 (KR) .................. 10-2013-0061800

(51) Int. Cl.
| | | |
|---|---|---|
| *G01N 33/50* | (2006.01) | |
| *C12N 5/079* | (2010.01) | |
| *G01N 33/569* | (2006.01) | |
| *C07K 14/005* | (2006.01) | |
| *C07K 14/52* | (2006.01) | |
| *C12N 7/00* | (2006.01) | |
| *A61K 39/245* | (2006.01) | |
| *A61K 39/12* | (2006.01) | |
| *A61K 31/00* | (2006.01) | |
| *A61K 38/20* | (2006.01) | |

(52) U.S. Cl.
CPC ....... *G01N 33/5047* (2013.01); *C12N 5/0621* (2013.01); *G01N 33/5044* (2013.01); *G01N 33/56994* (2013.01); *G01N 2333/05* (2013.01); *G01N 2800/16* (2013.01); *G01N 2800/7014* (2013.01)

(58) Field of Classification Search
CPC ...... A61K 9/0048; A61K 31/00; A61K 38/20; A61K 38/204; A61K 39/12; A61K 39/245; A61K 2039/55522; C12N 5/0621; C12N 7/00; C12N 2710/16234; C12N 2710/16271; C12N 2710/16252; C12N 2710/16262; C07K 14/005; C07K 14/52
See application file for complete search history.

(56) References Cited

U.S. PATENT DOCUMENTS

| | | | | |
|---|---|---|---|---|
| 8,785,395 B2* | 7/2014 | Prockop | ............... | A61K 9/0048 514/13.3 |
| 2011/0105426 A1* | 5/2011 | Pearlman | ............. | A61K 31/665 514/53 |
| 2012/0219602 A1* | 8/2012 | Flack | .................... | A61K 9/1075 424/400 |
| 2013/0189784 A1* | 7/2013 | Shukla | ..................... | C07K 7/08 435/375 |
| 2014/0294848 A1* | 10/2014 | Demore | ................ | A61K 38/13 424/139.1 |
| 2014/0314723 A1* | 10/2014 | Yim | ..................... | C12N 5/0621 424/93.7 |

FOREIGN PATENT DOCUMENTS

KR    10-2009-0083619 A    8/2009

OTHER PUBLICATIONS

Slobod KS, Sandlund JT, Spiegel PH, Haik B, Hurwitz JL, Conley ME, Bowman LC, Benaim E, Jenkins JJ, Stocks RM, Gan Y, Sixbey JW. Molecular evidence of ocular Epstein-Barr virus infection. Clin Infect Dis. Jul. 2000;31(1):184-8.*

Nanbo A, Terada H, Kachi K, Takada K, Matsuda T. Roles of cell signaling pathways in cell-to-cell contact-mediated Epstein-Barr virus transmission. J Virol. Sep. 2012;86(17):9285-96. Epub Jun. 20, 2012.*

Tran MT, Dean DA, Lausch RN, Oakes JE. Membranes of herpes simplex virus type-1-infected human corneal epithelial cells are not permeabilized to macromolecules and therefore do not release IL-1 alpha. Virology. Apr. 25, 1998;244(1):74-8.*

(Continued)

*Primary Examiner* — Rachel B Gill
(74) *Attorney, Agent, or Firm* — Revolution IP, PLLC

(57) ABSTRACT

The present invention relates to a cell model for diseases associated with corneal neovascularization by using Epstein Barr virus (EBV)-infected human corneal epithelial cells (HCECs). Provided are a method for preparing a cell model for diseases associated with corneal neovascularization by using EBV-infected HCECs, the method including: infecting HCECs with EBV; culturing the infected HCECs; and determining whether the cultured HCECs are infected with EBV. In addition, provided is a method for screening diseases associated with corneal neovascularization prepared by the cell model for diseases associated with corneal neovascularization.

5 Claims, 4 Drawing Sheets

(56) References Cited

OTHER PUBLICATIONS

Sugioka K, Drake JD, Fukuda M, Shimomura Y, Hwang DG. Susceptibility of human corneal endothelial cells to HSV-1 infection. Curr Eye Res. Oct. 2005;30(10):863-9. Erratum in: Curr Eye Res. Mar. 2007;32(3):299.*

Li H, Zhang J, Kumar A, Zheng M, Atherton SS, Yu FS. Herpes simplex virus 1 infection induces the expression of proinflammatory cytokines, interferons and TLR7 in human corneal epithelial cells. Immunology. Feb. 2006;117(2):167-76.*

Chen CC, Chang JH, Lee JB, Javier J, Azar DT. Human corneal epithelial cell viability and morphology after dilute alcohol exposure. Invest Ophthalmol Vis Sci. Aug. 2002;43(8):2593-602. Abstract.*

Qavi HB, Xu B, Green MT, Lusso P, Pearson G, Ablashi DV. Morphological and ultrastructural changes induced in corneal epithelial cells by HIV-1 and HHV-6 in vitro. Curr Eye Res. Jun. 1996;15(6):597-604.*

International Search Report for PCT/KR2013/011805 mailed Mar. 27, 2014 from Korean Intellectual Property Office.

Lin, Chin-Tamg et al., "Response of Nasopharyngeal Carcinoma Cells to Epstein-Barr Virus Infection In Vitro", Laboratory investigation, 2000, vol. 80, No. 8, pp. 1149-1160 See abstract and pp. 1157-1158.

Remeijer, Lies et al., "Human herpes simplex virus keratitis: the pathogenesis revisited", Ocular Immunology and Inflammation, 2004, vol. 12, No. 4, pp. 255-285 See entire document.

Pessina, Augusto et at, "Microbiological Risk Assessment in Stem Cell Manipulation", Critical Reviews in Microbiology. 2008, vol. 34, No. 1, pp. 10-12.

Lin,Zhen et al., "Detection of Murine Leukemia Virus in the Epstein-Barr Virus-Positive Human B-Cell Line JY, Using a Computational RNA-Seq-Based Exogenous Agent Detection Pipeline, PARSES", Journal of Virology, Jan. 11, vol. 686. No, 6. pp. 2970-2977 See entire document.

Sugita, Sunao et al., "Use of a Comprehensive Polymerase Chain Reaction System for Diagnosis of Ocular Infectious Diseases", Ophthalmology, Sep. 2013, vol. 120, No. 9, pp. 1761-1768 See entire document.

* cited by examiner

US 9,739,766 B2

CELL MODEL FOR NEOVASCULAR DISEASES USING EBV-INFECTED HUMAN CORNEAL EPITHELIAL CELLS

CROSS REFERENCE TO PRIOR APPLICATIONS

This application is a National Stage Application of PCT International Patent Application No. PCT/KR2013/011805 filed on Dec. 18, 2013, under 35 U.S.C. §371, which claims priority to Korean Patent Application No. 10-2013-0061800 filed on May 30, 2013, which are all hereby incorporated by reference in their entirety.

TECHNICAL FIELD

The present invention relates to a cell model for diseases associated with corneal neovascularization using Epstein Barr virus (EBV)-infected human corneal epithelial cells (HCECs).

BACKGROUND ART

Epstein-Barr virus (EBV) is a virus widely distributed in the world, belonging to the family Herpes, the subfamily Gammaherpes, and the genus *Lyphocryptovirus*. Once infected with EBV, EBV entering a genome of a B lymphocyte is not eliminated by an immune response. Accordingly, the B lymphocyte may be maintained in latent infection. In regard to the age associated with primary EBV infection depending on hygienic environments, about 80%, about 90%, and about 100% of positive rates are shown in 3-year-olds, about 20-years-old, and late 20s, respectively. The primary infection in childhood may cause asymptomatic or mild symptoms. However, the primary injection in adolescence may cause infectious mononucleosis (IM) in some cases, or chronic EBV infection in other cases. In addition, in a re-activation process of EBV having latent infection, opportunistic B cell lymphoma, Burkitt's lymphoma (BL), or nasopharyngeal carcinoma (NPC) may be caused. It is not well known why the disease incidence is different depending on the primary infection ages, but it is assumed that such difference may exist depending on maturity of a biological immune mechanism. EBV is an important carcinogen that causes many neoplastic disorders, and cells for lytic infection stimulate the growth of EBV-associated malignant tumors. Such phenomenon above may be related to an increase in angiogenesis EBV infection is rare in eye retina, but in the actual clinical practice, EBV-associated retinitis have been reported as one of complications of chronic active EBV infection. It is known that angiogenesis accompanies subsequent retinal necrosis.

Angiogenesis is a phenomenon of forming new blood vessels from existing blood vessels. It has known that angiogenesis is highly involved in crisis or development of diseases, such as malignant (solid) neoplasm, diabetic retiniopathy, senile macular degeneration, and inflammatory disease, e.g., rheumatoid arthritis. In addition, in consideration of metastasis that has become a major problem on cancer treatment, angiogenesis is an important step in terms of ensuring a path of metastasis. As such, angiogenesis is observed in a variety of lesions and may promote progress in each of the conditions. Thus, it is urgent to development a model applicable to evaluate angiogenesis and drug efficacy during the development of various drugs. In particular, the development of cell models has advantages of consuming a significantly lower cost compared with a cost required for clinical models and models for animal tests, and obtaining results by easy treatment, thereby having significantly high effectiveness.

Meanwhile, the Korean Patent No. 10-2008-0009530 (published on Jan. 30, 2008) discloses a method for screening an angiogenesis inhibitor, the method including screening an angiogenesis inhibitor through a contact between ubiquinone-binding protein (QP-C) of mitochondrial complex III and a test material. However, there is no reference to the cell model for diseases associated with corneal neovascularization using EBV-infected HIECs of the present invention.

Therefore, the present inventors have completed the present invention by indicating that the EBV-infected HCECs have a cell shape in a spindle form, are elongated, and show fibroblast-like characteristics and by confirming that expression of factors that are known to be involved in angiogenesis is relatively increased.

DETAILED DESCRIPTION OF THE INVENTION

Technical Problem

The present invention contrived as a means for solving the above-mentioned problems provides a method for preparing a cell model for diseases associated with corneal neovascularization by using Epstein Barr virus (EBV)-infected human corneal epithelial cells (HCECs).

The present invention also provides a cell model for diseases associated with corneal neovascularization prepared according to the method above.

The present invention also provides a method for screening a corneal angiogenesis therapeutic agent by using the cell model for diseases associated with corneal neovascularization.

Technical Solution

In order to accomplish the technical problems, the present invention provides a method for preparing a cell model for diseases associated with corneal neovascularization, the method including: infecting human corneal epithelial cells (HCECs) with Epstein Barr virus (EBV); culturing the infected HCECs; and determining whether the cultured HCECs are infected with the EBV.

In particular, the determination of whether the cultured HCECs are infected with the EBV is characterized by confirming expression of at least one protein selected from the group consisting of EBNA1, EBNA2, EBNA3A, and LMP1, and diseases associated with corneal neovascularization preferable include corneitis, corneal ulcer, or pterygium, that are caused by contact lenses and various inflammation, but are not limited thereto.

In addition, the present invention also provides a cell model for diseases associated with corneal neovascularization prepared according to the method above.

In addition, the present invention also provides a method for screening a therapeutic agent for diseases associated with corneal neovascularization, the method including: preparing a cell model for diseases associated with corneal neovascularization according to the method above; administering a therapeutic agent candidate to the cell model for diseases associated with corneal neovascularization; and measuring therapeutic effects of the therapeutic agent candidate.

Advantageous Effects of the Invention

The present invention relates to a cell model for diseases associated with corneal neovascularization by using Epstein Barr virus (EBV)-infected human corneal epithelial cells (HCECs). In the present invention, the EBV-infected HCECs are indicated to have a cell shape in a spindle form, are elongated, and show fibroblast-like morphology, and a relative increase in expression of factors that are known to be involved in angiogenesis is confirmed. Therefore, the cell model of the present invention can be easily used to discover the corneal angiogenesis mechanisms.

BEST MODE

Figure 1:
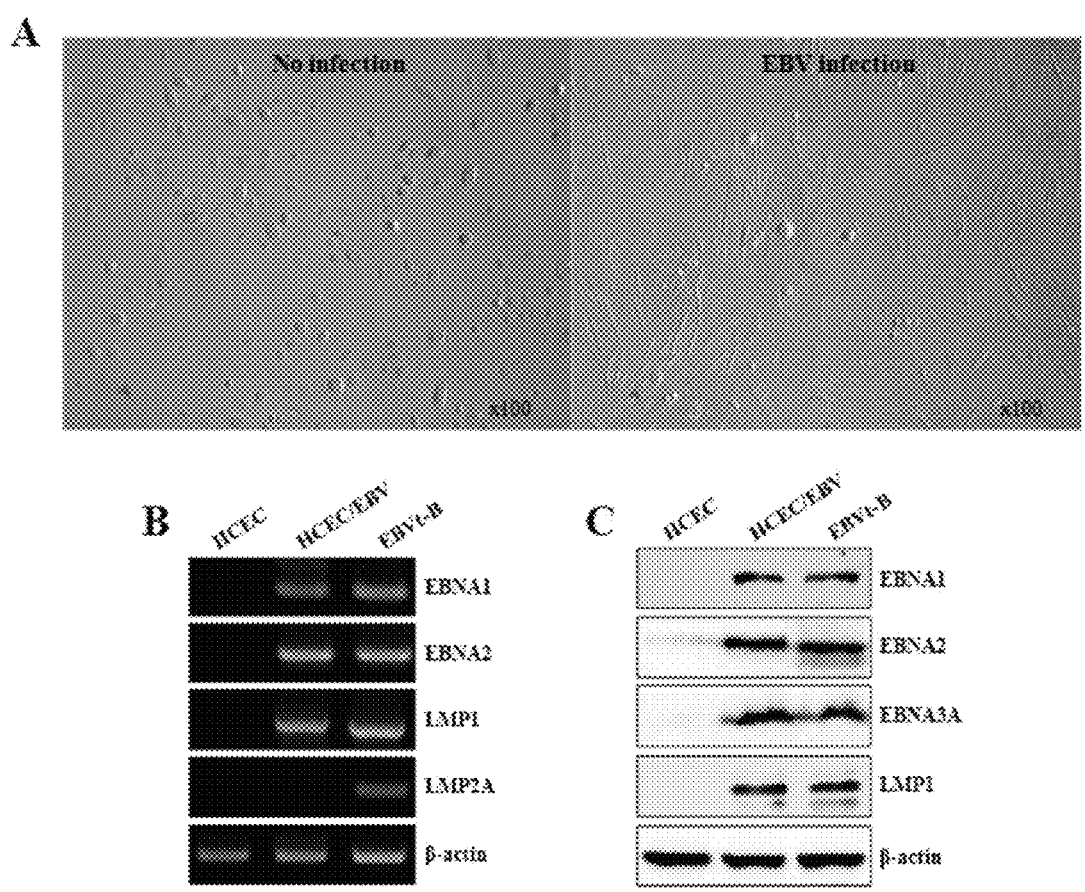
FIG. 1 shows experimental results obtained after infecting human corneal epithelial cells (HCECs) with Epstein Barr virus (EBV), the results used to detect cellular changes and determine whether the HCECs are infected with EBV. Diagram A of FIG. 1 shows results representing cell morphology after the infection; Diagram B of FIG. 1 shows results obtained by RT-PCR for confirming expression of EBV mRNAs (where EBV-transformed B cells are used as a positive control); and Diagram C of FIG. 1 shows results obtained by the western blot for confirming expression of EBV proteins.

In order to accomplish the technical problems, the present invention provides a method for preparing a cell model for diseases associated with corneal neovascularization, the method including: infecting human corneal epithelial cells (HCECs) with Epstein Barr virus (EBV); culturing the infected HCECs; and determining whether the cultured HCECs are infected with the EBV.

In particular, the determination of whether the cultured HCECs are infected with the EBV is characterized by confirming expression of at least one protein selected from the group consisting of EBNA1, EBNA2, EBNA3A, and LMP1, and diseases associated with corneal neovascularization preferable include corneitis, corneal ulcer, or pterygium, that are caused by contact lenses and various inflammation, but are not limited thereto.

In addition, the present invention also provides a cell model for diseases associated with corneal neovascularization prepared according to the method above.

The cell model of the present invention is not particularly limited, and may be prepared in any form as long as it is suitable for evaluation of pharmacological efficacy of target drugs in studies on treatment of diseases associated with corneal neovascularization. Target cell lines to which EBV is introduced in the present invention may preferable include HCECs, but are not limited thereto.

In addition, the present invention also provides a method for screening a therapeutic agent for diseases associated with corneal neovascularization, the method including: preparing a cell model for diseases associated with corneal neovascularization according to the method above; administering a therapeutic agent candidate to the cell model for diseases associated with corneal neovascularization; and measuring a therapeutic effect of the therapeutic agent candidate.

The therapeutic agent candidate for diseases associated with corneal neovascularization used herein refers to any substance that is expected to have therapeutic effects on diseases associated with corneal neovascularization and can be used as a target in experiments for measuring therapeutic effects of the therapeutic agent candidate. A substance that is applicable to animal experiments, is capable of measuring therapeutic effects, and is a material obtained from a natural substance or artificially synthesized may be used, and a type of the substance is not limited.

MODE OF THE INVENTION

Hereinafter, the present invention will be described in detail by referring to Examples below, but is not limited thereto.

<Example 1> Preparation of EBV-Infected HCECs and Detection of EBV-Associated Molecules in the EBV-Infected HCECs 1. Preparation of EBV-Infected HCECs EBV supernatant stock was prepared from an EBV B95-8 cell line (ATCC). Corneal epithelial cells were added to EBV stock supernatant, and then, incubated for 2 hours at 37° C. The resulting product was added to a keratinocyte serum-free medium (Gibco) ($3 \times 10^4$ cells/ml), and the cultures obtained therefrom were incubated for 1 day to 4 weeks.

2. Cell Culture

HCECs were purchased from the Gibco. Cells were maintained in a keratinocyte serum-free medium, supplemented with Bovine Pituitary Extract (BPE, Gibco) and human epidermal growth factor (EGF, Gibco) at 37° C. in 5% $CO_2$. EBV-transformed B cells were used as a positive control.

3. RT-PCR

Total RNAs were isolated using an RNeasy Mini kit (Qiagen), and then, transcribed into cDNA using oligo (dT) primers and reverse transcriptases. PCR products were amplified using specific primer sets (Bioneer) (see Table 1) and Prime Taq Premix (GeNet Bio), analyzed by agarose gel electrophoresis, and visualized with ethidium bromide under UV light using the multiple Gel DOC system (Fujifilm) to confirm bands formed on the agarose gel.

TABLE 1

Specific primer sequences used for RT-PCR are as follows.

| | Primers, 5' → 3' | |
| --- | --- | --- |
| Target | Sense | Antisense |
| EBNA1 | GAG CGG GGA GAT AAT GTA CA | TAA AAG ATG GCC GGA CAA GG |
| EBNA2 | AAC CCT CTA AGA CTC AAG GC | ACT TTC GTC TAA GTC TGC GG |

TABLE 1-continued

Specific primer sequences used for RT-PCR are as follows.

Primers, 5' → 3'

| Target | Sense | Antisense |
|---|---|---|
| LMP1 | CAC GAC CTT GAG AGG GGC CCA | GCC AGA TGG TGG CAC CAA GTC |
| LMP2A | ATG ACT CAT CTC AAC ACA TA | CAT GTT AGG CAA ATT GCA AA |
| IL-8 | ATG ACT TCC AAG CTG GCC GTG GCT | TCT CAG CCC TCT TCA AAA ACT TCT C |
| IL-6 | GTG TTG CCT GCT GCC TTC CCT G | CTC TAG GTA TAC CTC AAA CTC CAA |
| TGF-β | GGA CAC CAA CTA TTG CTT CAG | TCC AGG CTC CAA ATG TAG G |
| Hif-1α | TGA TTG CAT CTC CAT CTC CTA CC | GAC TCA AAG CGA CAG ATA ACA CG |
| VEGF | AGG AGG GCA GAA TCA TCA CG | CAA GGC CCA CAG GGA TTT TCT |
| STAT3 | ACC TGC AGC AAT ACC ATT GAC | AAG GTG AGG GAC TCA AAC TGC |
| MCP-1 | AAT GCC CCA GTC ACC TGC TGT TAT | GCA ATT TCC CCA AGT CTC TGT ATC |
| N-cadherin | CAC CCA ACA TGT TTA CAA TCA ACA ATG AGA C | CTG CAG CAA CAG TAA GGA CAA ACA TCC TAT T |
| E-cadherin | GAC GCG GAC GAT GAT GTG AAC | TTG TAC TGTR TGT GGA TTG AAG |
| Vimentin | GGA AGA GAA CTT TGC CGT TGA A | GTG ACG AGC CAT TTC CTC CTT |
| S100A4 | TCA GAA CTA AAG GAG CTG CTG ACC | TTT CTT CCT GGG CTG CTT ATC TGG |
| α-SMA | ATC ACC ATC GGA AAT GAA CG | CTG GAA GGT GGA CAG AGA GG |
| Snail | CAG ATG AGG ACA GTG GGA AAG G | ACT CTT GGT GCT TGT GGA GCA G |
| Fibronectin | CCG TGG GCA ACT CTG TC | TGC GGC AGT TGT CAC AG |
| MMP2 | TGG CAA GTA CGG CTT CTG TC | TGG CAA GTA CGG CTT CTG TC |
| MMP9 | TGC GCT ACC ACC TCG AAC TT | GAT GCC ATT GAC GTC GTC CT |
| β-actin | ATC CAC GAA ACT ACC TTC AA | ATC CAC ACG GAG TAC TTG C |

4. Western Blot

Cells were collected and lysed in NP-40 buffer (Elpis Biotech) containing a protease inhibitor cocktail and a phosphatase inhibitor cocktail (Sigma-Aldrich). Total cell lysates were subjected to SDS-PAGE. Proteins separated therefrom were transferred to nitrocellulose membranes (Millipore), which was then blocked with 5% skim milk, and conventional immune-blot was performed using several antibodies. Then, immune-reactive proteins were detected with an ECL kit (Advansta) and the multiple Gel DOC system. The following primary Abs were used: phospho-STAT3 ($Tyr^{705}$), STAT3, Hif-1α, MMP-2, MMP-9, phospho-Akt ($Ser^{473}$), Akt, phospho-ERK1/2 ($Thr^{202}/Tyr^{204}$),) ERK1/2, E-cadherin, N-cadherin, β-catenin, Vimentin, Snail, TCF8/ZEB1, and β-actin from Cell Signaling Technology (Beverly, Mass.); EBNA-2, EBNA-3A, LMP-1, Ang-1, and VEGF from Santa Cruz Biotechnology; and EBNA-1 from Thermo Scientific. Densitometry analysis was performed with ImageJ 1.38 software (National Institutes of Health).

5. Results

EBV can infect both B cells and epithelial cells. To infect with EBV in the HCECs, the present inventors first examined the presence of the well known receptor CD21 on the HCECs using flow cytometry. However, the CD21 was not expressed in the HCECs. In spite of that, the present inventors established EBV-containing HCECs showing latency type III. Typically, the EBV transformation process in B cells is established at almost 4 weeks, and the early signs of transformation (e.g., increased cell size, cell aggregation, and sudden increment in growth) are observed after 1 to 3 weeks. In this situation, the present inventors found that EBV-infected HCECs changed their shapes from cuboidal and ovoidal to spindle at least within 1 week compared to non-infected cells. In particular, after 3 weeks of exposure to EBV, the attached cells completely resembled mesenchymal fibroblast-like spindle-shaped cells (see FIG. 1A). This means that the EBV-infected HCECs exhibit a spindle-shaped, elongated, fibroblast-like morphology, and are bipolar or multipolar. To confirm the EBV infection on the HCECs, the present inventors performed RT-PCR and the western blot for analysis of viral transcripts and proteins. In non-exposed HCECs, the EBV-related gene transcripts and proteins were not observed, indicating that the HCECs are free from EBV injection (see FIGS. 1B and 1C). After exposure to EBV, expression of EBNA1, EBNA2, EBNA3A, and LMP1, except LMP2A, was observed in the EBV-infected HCECs (see FIGS. 1B and 1C).

<Example 2> Production of Various Pro-Inflammatory and Pro-Angiogenesis in HCECs Promoted by EBV Infection 1. ELISA Assay After culturing cells for 24 hours, the culture supernatant was collected and amounts of IL-6, IL-8, and MCP-1 secreted by HCECs or EBV-infected HCECs were quantified by the Single Analyte ELISArray Kit (Qiagen). VEGF and TGF-β were quantified by the Single cytokine ELISA assay Kit (R&D systems). The results obtained therefrom are expressed as the average of the number of biological replicates±standard deviation (SD).

2. Results

Figure 2:
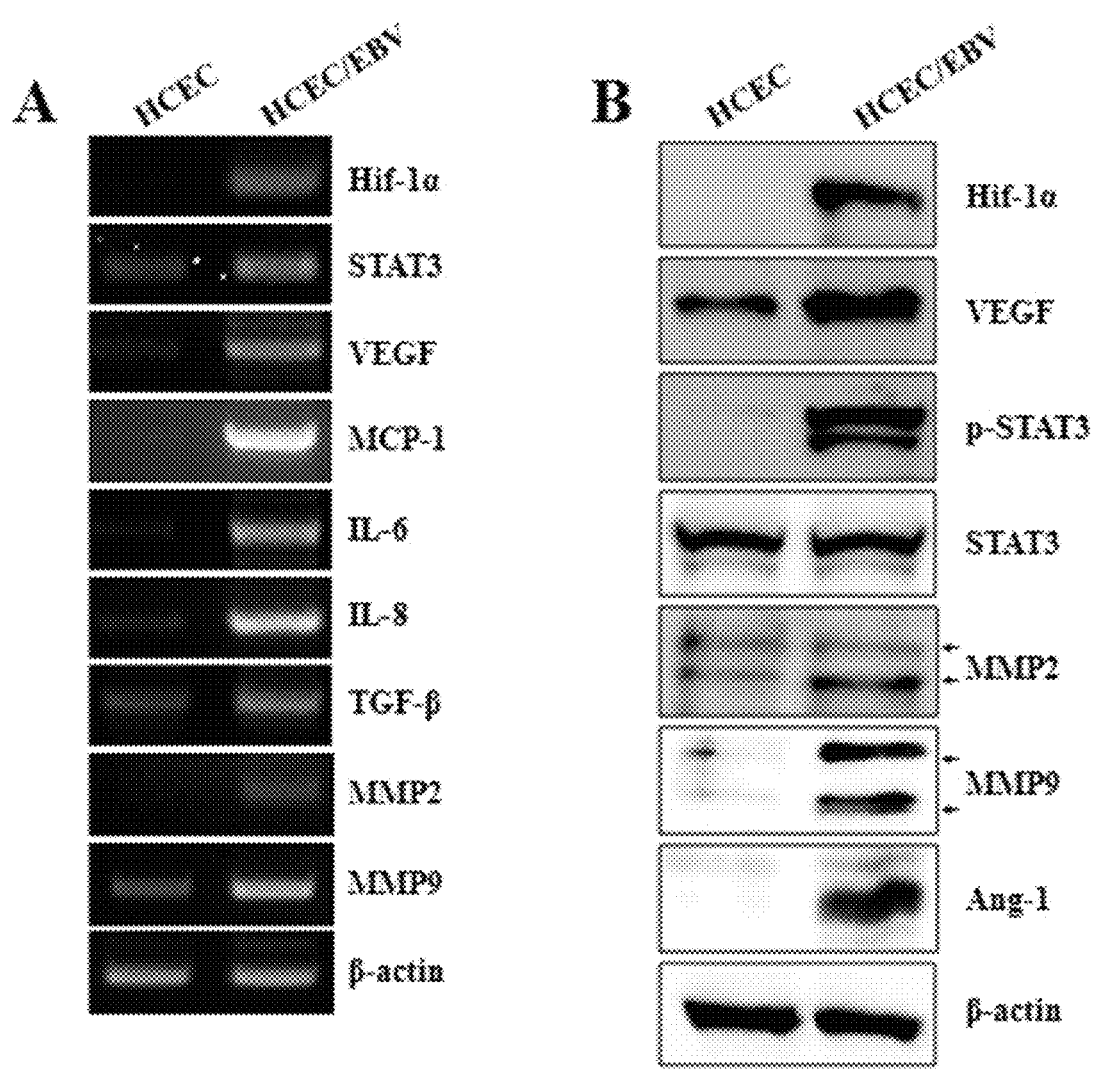
FIG. 2 shows results obtained by RT-PCR and the western blot for confirming changes in expression of angiogenesis-associated transcription factors and signaling molecules in the EBV-infected HCECs. Diagram A of FIG. 2 shows results for confirming increased expression of angiogenesis-related factors, e.g., IL-6, IL-8, VEGF, MCP-1, and TGF-beta, after the infection, and Diagram B of FIG. 2 shows results obtained by the western blot for confirming expression of representative angiogenesis factors, e.g., STAT-3, VEGF, and angiotensin-1 (Ang-1), at protein levels.
Figure 3:
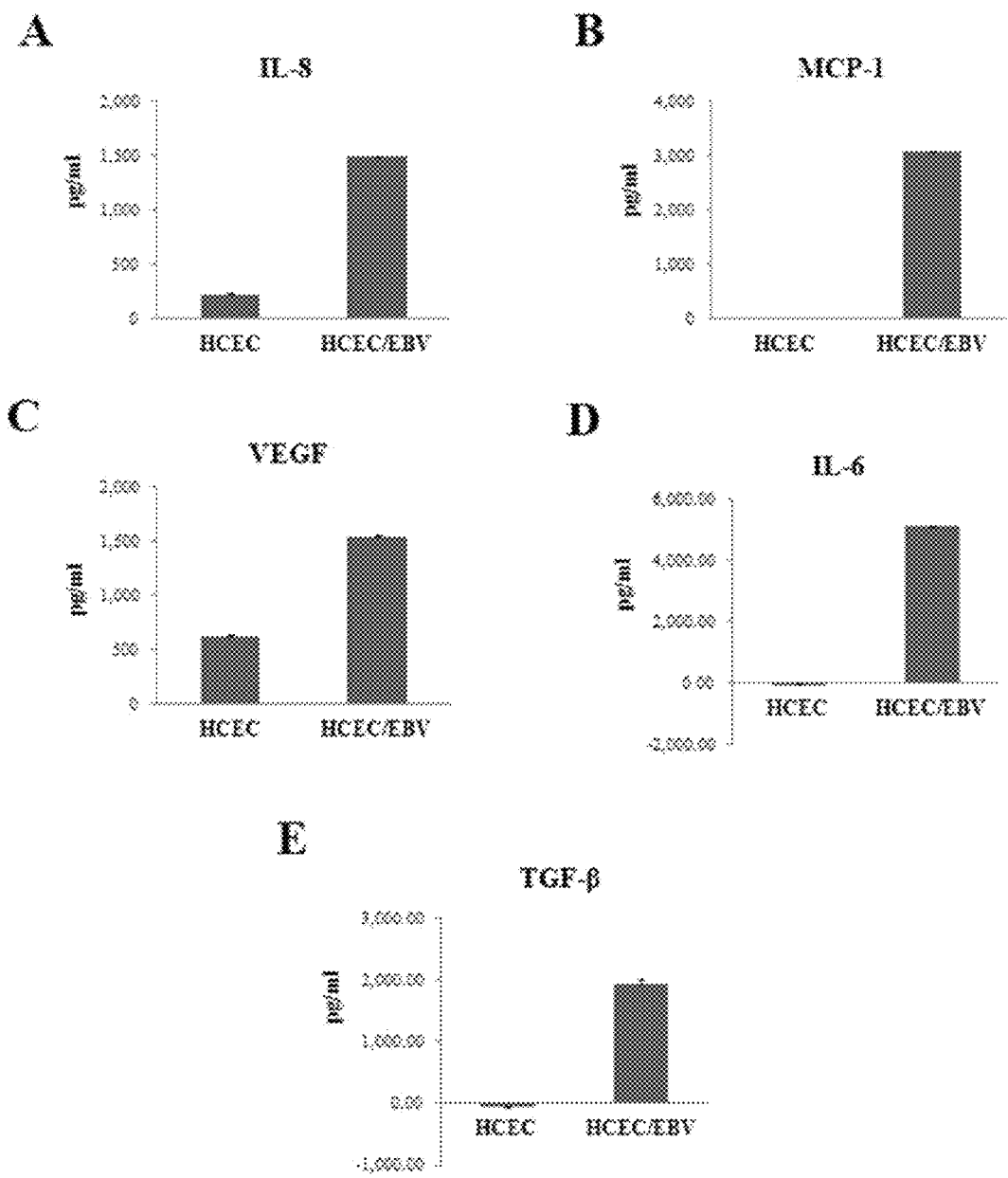
FIG. 3 shows experimental results obtained for by ELISA for confirming whether increased expression of angiogenesis-related factors, e.g., IL-8, MCP-1, VEGF, IL-6, and TGF-beta, in the EBV-infected HCECs influences increased secretion of the factors into a culture medium.

As reported in previous studies, viral infection including EBV evokes the production of cytokines or chemokines in immune cells and tumor cells. In addition, the present inventors supposed that differentiation of HCECs into fibroblast-like cells by EBV infection is related to their capability to induce growth and angiogenic factors. These factors, through autocrine and paracrine actions, promote the growth of various cells including tumor cells and induce blood vessel developments that supply nutrients and oxygen necessary for tumor growth. To test this contention, the present inventors analyzed mRNA levels and protein levels of pro-inflammatory cytokines and angiogenic factors by using RT-PCR and the western blot analysis. Secretion levels of these factors were analyzed quantitatively in the culture supernatant of the HCECs or the EBV-infected HCEC cells using Single Analyte ELISArray kit. As shown in FIG. 2, pro-angiogenic and growth factors, e.g., IL-6, IL-8, VEGF, MCP-1, and TGF-β, were more significantly expressed after the EBV infection as compared to non-infected cells. In particular, the secretion levels of MCP-1, IL-6, and TGF-β were also dramatically enhanced in the EBV-infected HCECs and IL-8 and VEGF were also sufficiently secreted in the EBV-infected HCECs (see FIG. 3). In addition, the secretion of TGF-β, which was well known to induce EMT, was increased in the EBV-infected HCECs, whereas non-infected cells did not produce TGF-β. To examine the molecules triggering the production of pro-inflammatory and pro-angiogenic factors in the EBV-infected HCECs, the present inventors noticed Hif-1α and STAT3, which were related to neovascularization. The expression levels of Hif-1α, p-STAT3, and Ang-1 were considerably enhanced in the EBV-infected HCECs as compared to non-infected cells. Furthermore, STAT3 target genes, such as MMP2 and MMP9, were also up-regulated after the EBV infection (see FIGS. 2A and 2B).

<Example 3> Induction of Phenotype Changes in HCECs Upon EBV Infection

EMT is a cellular transdifferentiation program that enables polarized, immotile epithelial cells to convert to motile mesenchymal cells. This program has been implicated in promoting dissemination of single malignant cells from primary epithelial tumors and invasion.

Figure 4:
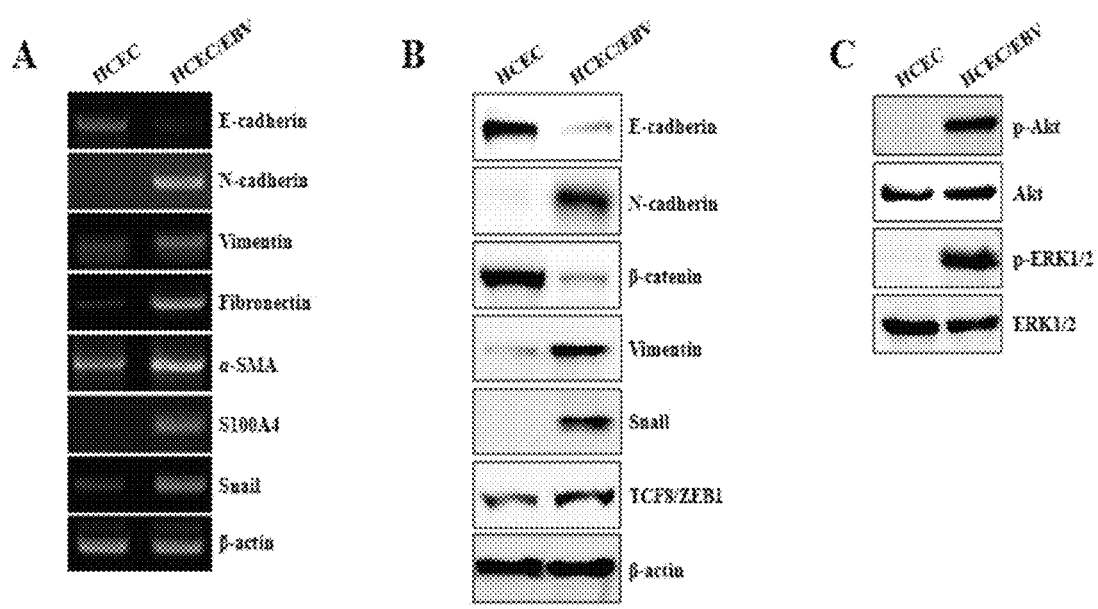
FIG. 4 shows results for confirming whether the EBV-infected HCECs are subjected to epithelial-mesenchymal transition (EMT).

Since differentiation into fibroblast-like cells and the secretion of TGF-β by the EBV infection in the HCECs were similar to EMT, the present inventors speculated that the EBV-infected HCECs were subjected to EMT. To corroborate this, the present inventors investigated whether expression of EMT markers were changed after EBV infection using RT-PCR analysis. In general, the HCECs were shown to express dominantly E-cadherin and β-catenin, while they were negative or low level for the expression of N-cadherin, vimentin, α-SMA, S100A4, TCF8/ZEB1, fibronectin, and Snail (see FIGS. 4A and 4B). Surprisingly, the EBV-infected HCECs expressed practically no detectable epithelial markers, E-cadherin and β-catenin. In contrast, these cells significantly expressed mesenchymal markers, N-cadherin, vimentin, α-SMA, S100A4, TCF8/ZEB1, fibronectin, and Snail (FIGS. 4A and 4B). Therefore, the results obtained therefrom suggest that the EBV infection in the HCECs influences initiation of EMT formation.

PI3K/Akt and ERK1/2 activation plays a pivotal role in cell migration and the dynamic regulation of the cytoskeleton in many physiological functions including TGF-β-induced EMT. Therefore, the present inventors examined the possible involvement of Akt and ERK1/2 in the EBV infection-induced EMT in the HCECs. Consequently, phosphorylation of Akt and ERK1/2 were remarkably increased after the EBV infection (see FIG. 4C). These results suggest that Akt and ERK1/2 may play a role in EBV-induced EMT in the HCECs.

The invention claimed is:

1. A method for preparing a cell model for diseases associated with corneal neovascularization, the method comprising:
    infecting isolated human corneal epithelial cells (HCECs) with Epstein Barr virus (EBV);
    culturing the infected HCECs with keratinocyte serum-free medium in vitro, wherein the keratinocyte serum-free medium includes bovine pituitary extract and human epidermal growth factor; and
    determining whether the cultured HCECs are infected with the EBV,
    wherein a diseases associated with corneal neovascularization is selected from the group consisting of corneitis, corneal ulcer, and pterygium,
    wherein a cell shape of the EBV-infected HCECs is changed from cuboidal and ovoidal to spindle at least within 1 week compared to non-infected cells, and the EBV-infected HCECs express at least one cytokine selected from the group consisting of MCP-1, IL-6, and TGF-β.

2. The method of claim 1, wherein the determination of whether the cultured HCECs are infected with the EBV is characterized by confirming expression of at least one protein selected from the group consisting of EBNA1, EBNA2, EBNA3A, and LMP1.

3. A cell model for diseases associated with corneal neovascularization prepared according to the method of claim 1.

4. A method for screening a therapeutic agent for diseases associated with corneal neovascularization, the method comprising:
    preparing a cell model for diseases associated with corneal neovascularization according to the method of claim 1;

administering a therapeutic agent candidate to the cell model for diseases associated with corneal neovascularization; and measuring a therapeutic effect of the therapeutic agent candidate.

5. A cell model for diseases associated with corneal neovascularization prepared according to the method of claim 2.

* * * * *